(12) United States Patent
Schneider et al.

(10) Patent No.: US 10,004,851 B2
(45) Date of Patent: Jun. 26, 2018

(54) SELF-INJECTION DEVICE WITH INDICATOR FOR INDICATING PROPER CONNECTION OF COMPONENTS

(71) Applicant: Becton, Dickinson and Company, Franklin Lakes, NJ (US)

(72) Inventors: Jared Schneider, Cranston, RI (US); Mark Guarraia, Cranston, RI (US); Margaux Boyaval, Warwick, RI (US); Ryan Shafer, Whitinsville, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days. days.

(21) Appl. No.: 14/394,039

(22) PCT Filed: Apr. 12, 2013

(86) PCT No.: PCT/US2013/036405
§ 371 (c)(1),
(2) Date: Oct. 10, 2014

(87) PCT Pub. No.: WO2013/155435
PCT Pub. Date: Oct. 17, 2013

(65) Prior Publication Data
US 2015/0080807 A1 Mar. 19, 2015

Related U.S. Application Data

(60) Provisional application No. 61/624,218, filed on Apr. 13, 2012.

(51) Int. Cl.
A61M 5/24 (2006.01)
A61M 5/315 (2006.01)
(Continued)

(52) U.S. Cl.
CPC ............... *A61M 5/24* (2013.01); *A61M 5/20* (2013.01); *A61M 5/3155* (2013.01);
(Continued)

(58) Field of Classification Search
CPC ........ A61M 5/24; A61M 5/20; A61M 5/3155; A61M 2005/2006; A61M 2005/2403;
(Continued)

(56) References Cited

U.S. PATENT DOCUMENTS 5,873,861 A 2/1999 Hitchins et al.
6,001,082 A 12/1999 Dair et al.
(Continued)

FOREIGN PATENT DOCUMENTS

CN 101184521 A 5/2008
CN 102413856 A 4/2012
(Continued)

*Primary Examiner* — Lauren P Farrar
(74) *Attorney, Agent, or Firm* — Dickinson Wright, PLLC

(57) ABSTRACT

A self-injection device includes a visual indicator for visually indicating that a main body and a cartridge holder are properly connected to each other. In one embodiment, the visual indicator includes a visual marking on the cartridge holder and a visual marking on the main body, such that when the cartridge holder and the main body are properly connected, the visual markings are aligned with each other. A self-injection device that includes an indicator for a dose window is also disclosed.

14 Claims, 9 Drawing Sheets

(51) Int. Cl.
    *A61M 5/20*      (2006.01)
    *A61M 5/31*      (2006.01)

(52) U.S. Cl.
    CPC ............... *A61M 2005/2006* (2013.01); *A61M 2005/2403* (2013.01); *A61M 2005/2485* (2013.01); *A61M 2005/2488* (2013.01); *A61M 2005/3126* (2013.01); *A61M 2205/58* (2013.01); *A61M 2205/583* (2013.01); *A61M 2205/585* (2013.01)

(58) Field of Classification Search
    CPC .. A61M 2005/2485; A61M 2005/3126; A61M 2205/58; A61M 2205/583; A61M 2205/585
    See application file for complete search history.

(56) References Cited

U.S. PATENT DOCUMENTS

| | | | |
|---|---|---|---|
| 6,210,369 B1 * | 4/2001 | Wilmot | A61M 5/2033 604/157 |
| 7,195,616 B2 * | 3/2007 | Diller | A61M 5/31566 604/207 |
| 2006/0229562 A1 | 10/2006 | Marsh | |
| 2008/0269688 A1 | 10/2008 | Colucci et al. | |
| 2009/0069752 A1 * | 3/2009 | Raj | A61M 5/3202 604/192 |
| 2009/0157041 A1 * | 6/2009 | Pettis | A61M 5/28 604/506 |
| 2010/0160894 A1 | 6/2010 | Julian | |
| 2010/0168677 A1 * | 7/2010 | Gabriel | A61M 5/31551 604/189 |
| 2011/0313350 A1 * | 12/2011 | Krulevitch | A61M 5/24 604/65 |
| 2013/0131604 A1 * | 5/2013 | Avery | A61M 5/24 604/207 |
| 2013/0313823 A1 * | 11/2013 | Holmqvist | A61M 5/3129 285/330 |

FOREIGN PATENT DOCUMENTS

| | | |
|---|---|---|
| DE | 102007018696 A1 | 10/2008 |
| DE | 202008011175 U1 | 1/2010 |
| EP | 2774640 A1 | 9/2014 |
| JP | 2009-542334 | 12/2009 |
| WO | WO-9938554 A1 | 8/1999 |
| WO | WO-9964092 A1 | 12/1999 |
| WO | WO-2007107431 A1 | 9/2007 |
| WO | WO-2010112558 A1 | 10/2010 |
| WO | WO-2010139629 A1 | 12/2010 |
| WO | WO-2010139634 A1 | 12/2010 |
| WO | WO-2011/008190 A1 | 1/2011 |
| WO | WO-2011039209 A1 | 4/2011 |
| WO | WO-2011039211 A1 | 4/2011 |
| WO | WO-2011039219 A2 | 4/2011 |
| WO | WO-2011039228 A1 | 4/2011 |

* cited by examiner

SELF-INJECTION DEVICE WITH INDICATOR FOR INDICATING PROPER CONNECTION OF COMPONENTS

CROSS-REFERENCE TO RELATED APPLICATION

This application claims priority under 35 USC § 119(e) from U.S. Provisional Patent Application Ser. No. 61/624,218, filed on Apr. 13, 2012, the disclosure of which is incorporated herein by reference in its entirety.

FIELD OF THE INVENTION

The present invention relates generally to self-injection devices. More particularly, the present invention generally relates to a drug delivery pen having a visual indicator that alerts a user whether key components of the drug delivery pen are properly connected to each other.

BACKGROUND OF THE INVENTION

Insulin and other injectable medications are commonly administered with drug delivery pens, whereby a disposable pen needle assembly is attached to facilitate drug container access and allow fluid egress from the container through a needle into the patient.

The assembly and operation of a typical drug delivery pen are described in U.S. Patent Application Publication No. 2006/0229562 to Marsh et al., published on Oct. 12, 2006, which is hereby incorporated by reference in its entirety. Drug delivery pens typically include a dial function that can control the exact amount of dosage that is injected. However, the exactness of the dosage is based on the assumption that the main components of the drug delivery pen, namely a main body with a dosage dialing function and a medicament cartridge holder holding a liquid medicament cartridge, are connected together properly. A drive mechanism, such as a piston, extends from the main body against the medicament cartridge housed in the cartridge holder, and its movement is based on proper attachment of the main body to the cartridge holder. However, a proper connection between the main body and the cartridge holder may be lost due to user error or some form of vibration or unintended force that causes an unwanted partial separation between the main body and the cartridge holder.

Accordingly, a need exists for an improved drug delivery pen that can alert a user that key components thereof are not properly connected, which would result in an improper dosage of medicament being delivered to a user.

SUMMARY OF THE INVENTION

In accordance with an aspect of the present invention, a drug delivery pen is provided including a visual indicator for alerting a user that the main components are not properly attached together, which may result in an improper dosage of medicament being delivered to the user.

An objective of the present invention is to provide various embodiments of visual indicators that may be used for such purpose.

These and other objects are substantially achieved by providing a self-injection pen in the form of a drug delivery pen in which a main body having a dose dialing function and a cartridge holder are each provided with a marking, such that when the main body and the cartridge holder are properly connected, the respective markings align with each other to inform a user of a correct connection.

BRIEF DESCRIPTION OF THE DRAWINGS

The various objects, advantages and novel features of the exemplary embodiments of the present invention will be more readily appreciated from the following detailed description when read in conjunction with the appended drawings, in which.

DETAILED DESCRIPTION OF THE EXEMPLARY EMBODIMENTS

Figure 1:
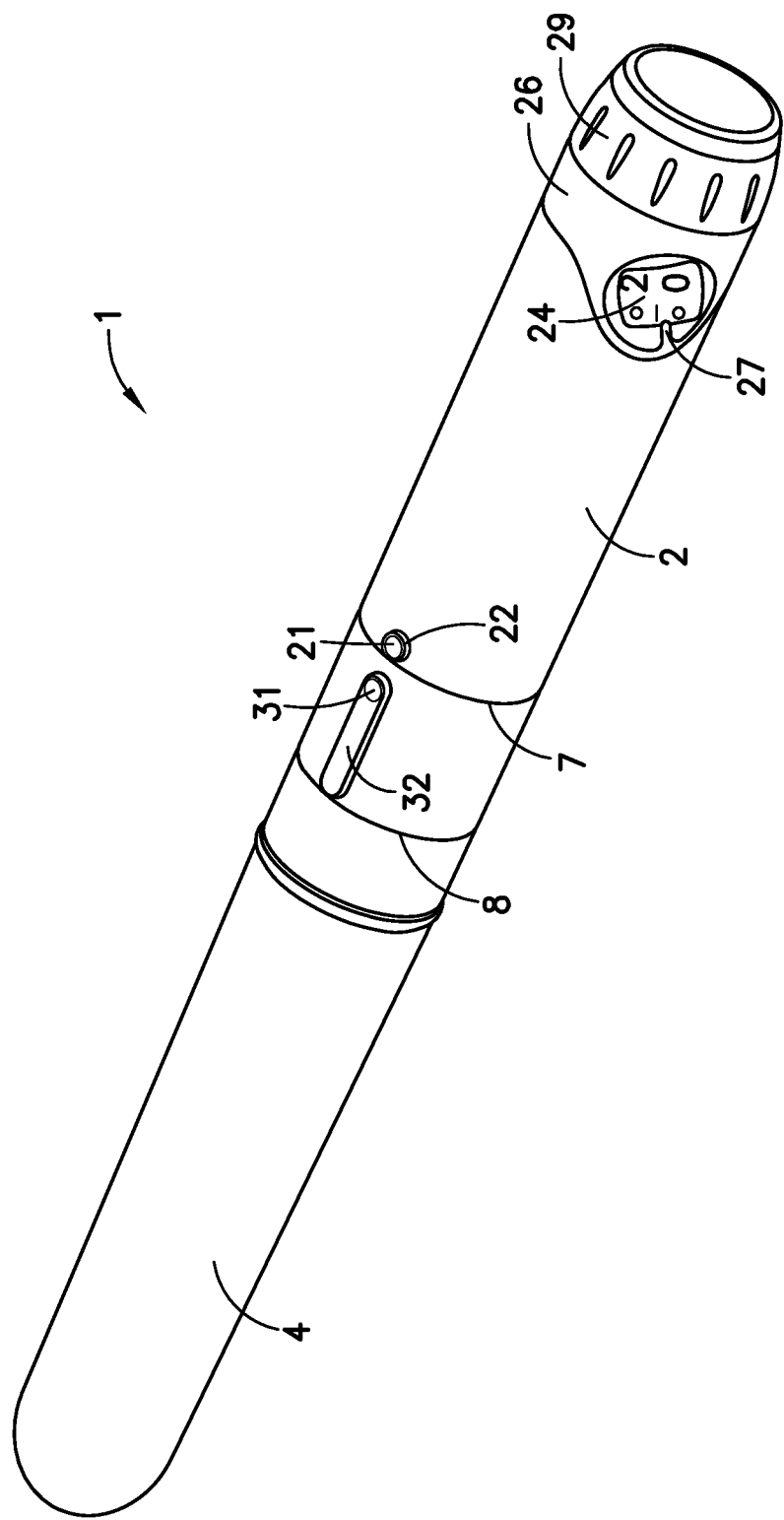
FIG. 1 is a perspective view of a drug delivery pen in accordance with an embodiment of the present invention.

FIGS. 1-4 disclose an embodiment of the self-injection device of the present invention. The self-injection device 1 includes a main body 2, a cartridge holder 3 and a cap 4. The cartridge holder 3 houses a disposable cartridge (not shown) containing liquid medicament, such as insulin. The cartridge holder 3 is secured to the main body 2, preferably via male and female threads on the main body 2 and the cartridge holder 3. The main body 2 includes a dose setting device 29, preferably in the form of a dial. The user rotates the dose setting device 29 to select the appropriate dosage for injection by matching the desired dosage to the corresponding measurement that is visible in a window 24, and then pushes the dose setting device 29 which causes a drive mechanism such as a piston (not shown) to act against a cartridge connected to an injection needle so that the desired amount of liquid medicament is forced out of the injection needle into the skin of a user.

The dose setting device 29 is calibrated on the assumption that the cartridge holder 3 is properly attached to the main body 2. However, if the cartridge holder 3 and the main body 2 are not properly attached, the user may not be able to receive the correct dosage of medicament. For instance, if the cartridge holder 3 is further apart from the main body 2 than it is in its nominal attachment position, a piston (not shown) actuated by the dose setting device 3 may travel a set distance which would not be sufficient to deliver the desired dosage due to the improper attachment of the cartridge holder 3 to the main body 2.

FIG. 1 illustrates the self-injection pen 1 with the cap 4 attached to the cartridge holder 3, and the cartridge holder 3 being properly connected to the main body 2. A proper connection between the main body 2 and the cartridge holder 3 is indicated when the indicator mark 21 on the main body 2 and the indicator mark 31 on the cartridge holder 3 are rotationally aligned with each other along the longitudinal length or axis of the self-injection device 1. In FIG. 1, only a portion of the cartridge holder 3 is visible due to the cap 4 being placed on the cartridge holder 3.

Figure 2:
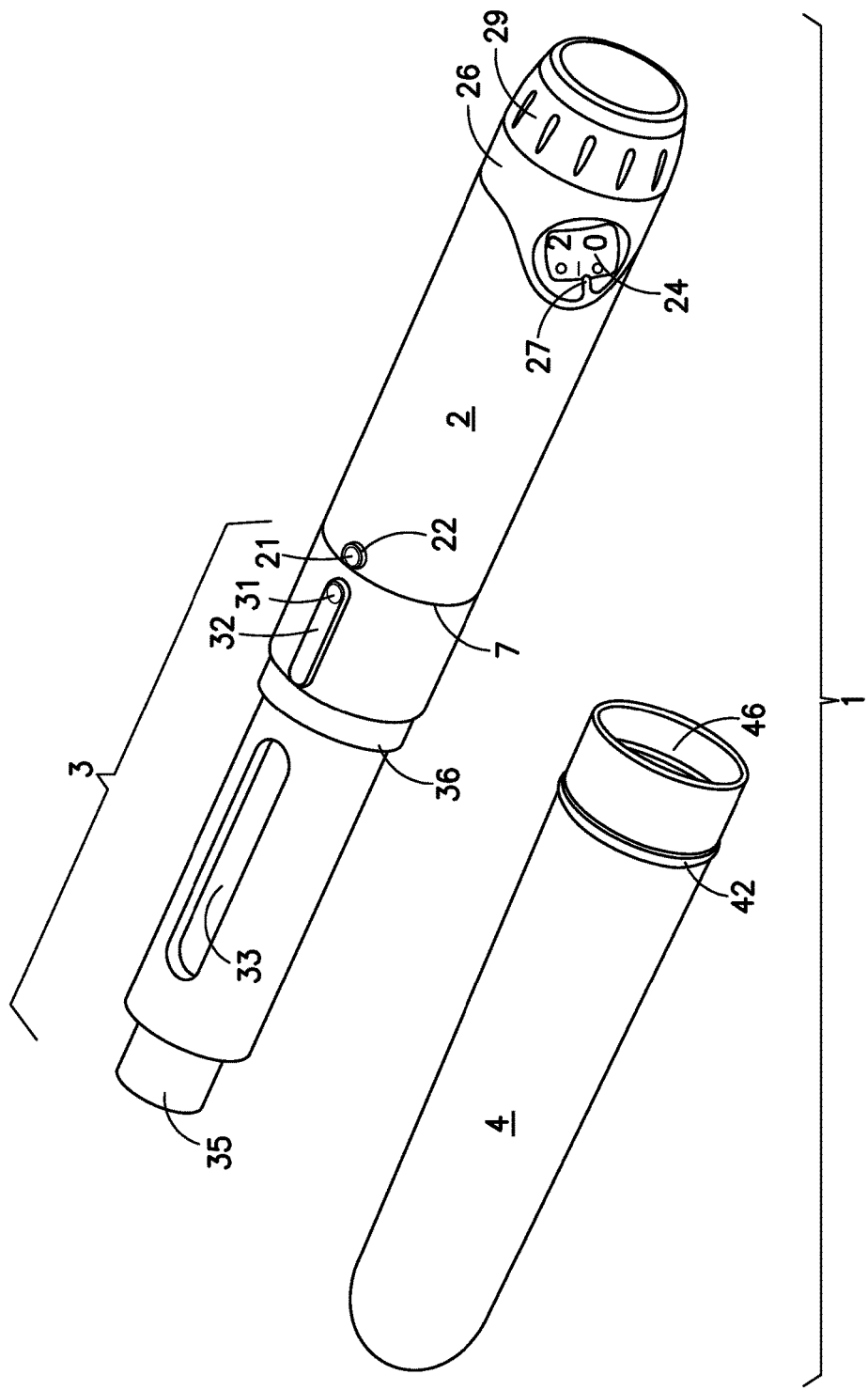
FIG. 2 is a perspective view of the drug delivery pen of FIG. 1 with its cap removed.

FIG. 2 illustrates the self-injection pen 1 of FIG. 1, with the cap 4 removed from the cartridge holder 3. The cartridge holder 3 includes a window opening 33 through which the liquid medicament cartridge (not shown) is visible when present. The cartridge holder 3 includes an injection needle receiving portion 35 at an open end, allowing attachment of an injection hub containing a penetrating needle cannula for piercing the cartridge and a needle for penetrating a user's skin, prior to use. The cartridge holder 3 includes a protruding outer ring 36 and the cap 4 includes a protruding inner ring 46. When the cap 4 is pushed on the cartridge holder 3, the respective rings 36, 46 engage and prevent further movement of the cap 4 against the cartridge holder 3. The cap 4 may include an outer ring 42 which assists a user to grip the cap 4 for attachment to and removal from the cartridge holder 3.

Figure 3:
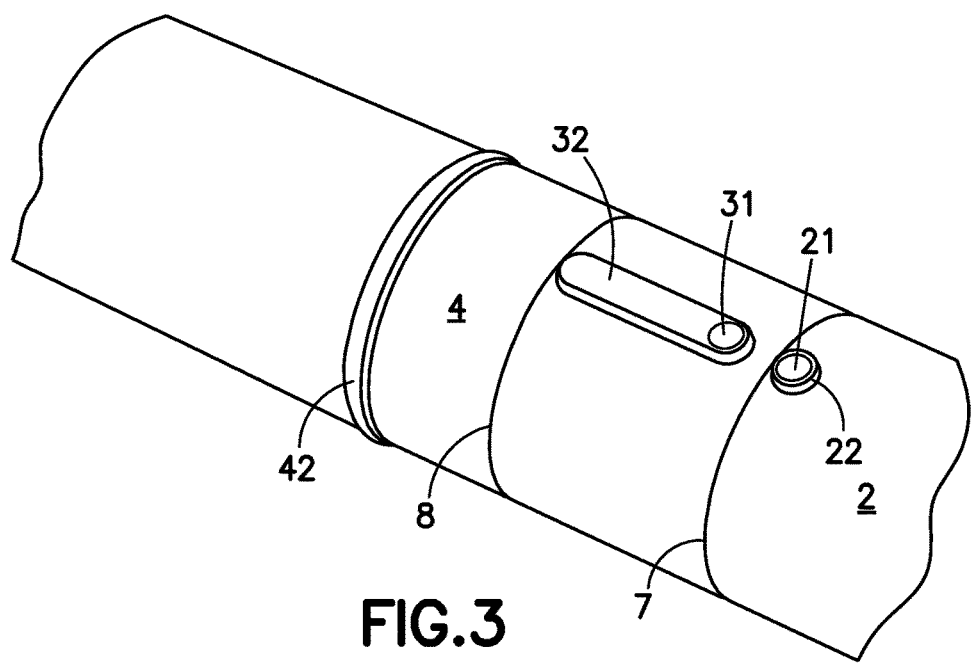
FIG. 3 is a close-up view of a visual indicator showing proper attachment of the medicament holder to the main body of the drug delivery pen of FIG. 1.

The self-injection pen 1 includes visual indicators 21, 22 and 31, 32 for indicating that the main body 2 and the cartridge holder 3 are properly connected together. As illustrated in FIGS. 2 and 3, the cartridge holder 3 includes a visual indicator in the form of indicia 31, as well as a raised longitudinal bar 32 on which the indicia 31 is positioned. The raised bar 32 also prevents full rotation or rolling of the self-injection pen 1 when the injection pen 1 is placed on a flat surface (e.g., a table). The main body 2 includes a visual indicator in the form of indicia 21 position on a raised portion 22. When the cartridge holder 3 and the main body 2 are properly attached together, preferably by being threaded onto one another, the indicia 21 and 31, as well as the raised portion 22 and the raised longitudinal bar 32, rotationally align in the direction of the longitudinal length or axis of the self-injection device, as illustrated in FIGS. 1-3. In the event that the cartridge holder 3 and the main body 2 are not properly attached together, the visual indicators 21, 22 and 31, 32 will not align properly in the manner illustrated in FIG. 2 (i.e., they may be rotationally and/or axially displaced from one another). The raised bar 32 and the raised portion 22 may assist visually-impaired users in determining whether the cartridge holder 3 is properly attached to the main body 2.

Line 7, illustrated in FIGS. 1-3, exemplifies the outer connection between the cartridge holder 3 and the main body 2. Line 8, illustrated in FIGS. 1 and 3, exemplifies the outer connection between the cap 4 and the cartridge holder 3.

FIG. 3 is a close-up view of the self-injection device 1 in which the cap 4 is attached to the cartridge holder 3 and the cartridge holder 3 is properly attached to the main body 2. As illustrated, the visual indicators for proper alignment in the form of the indicator marks 21, 31, as well as the raised portions 22, 32, indicate to a user, visually or by touch, that the cartridge holder 3 is properly attached to the main body 2.

Figure 4:
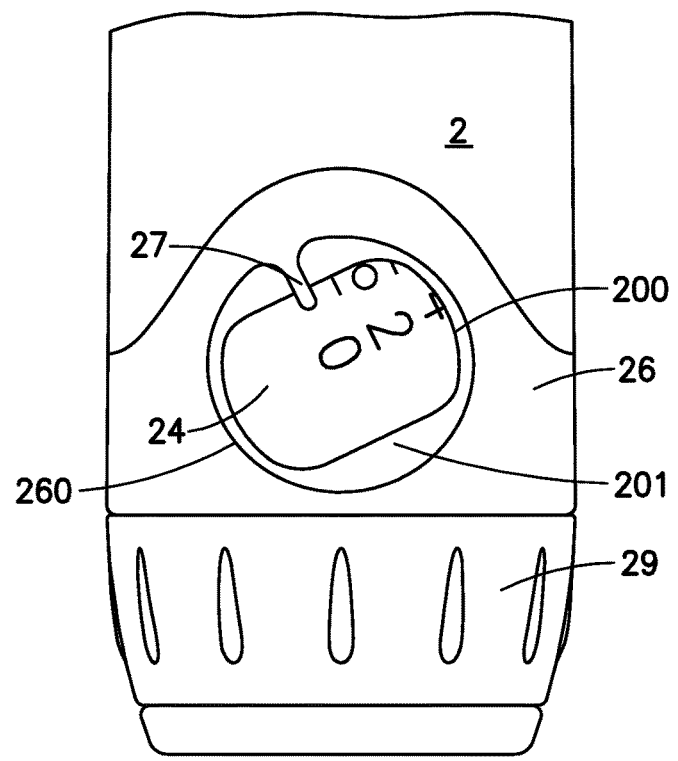
FIG. 4 is a close-up view of a display window for dosage of medicament to be delivered of the drug delivery pen of FIG. 1.
Figure 5:
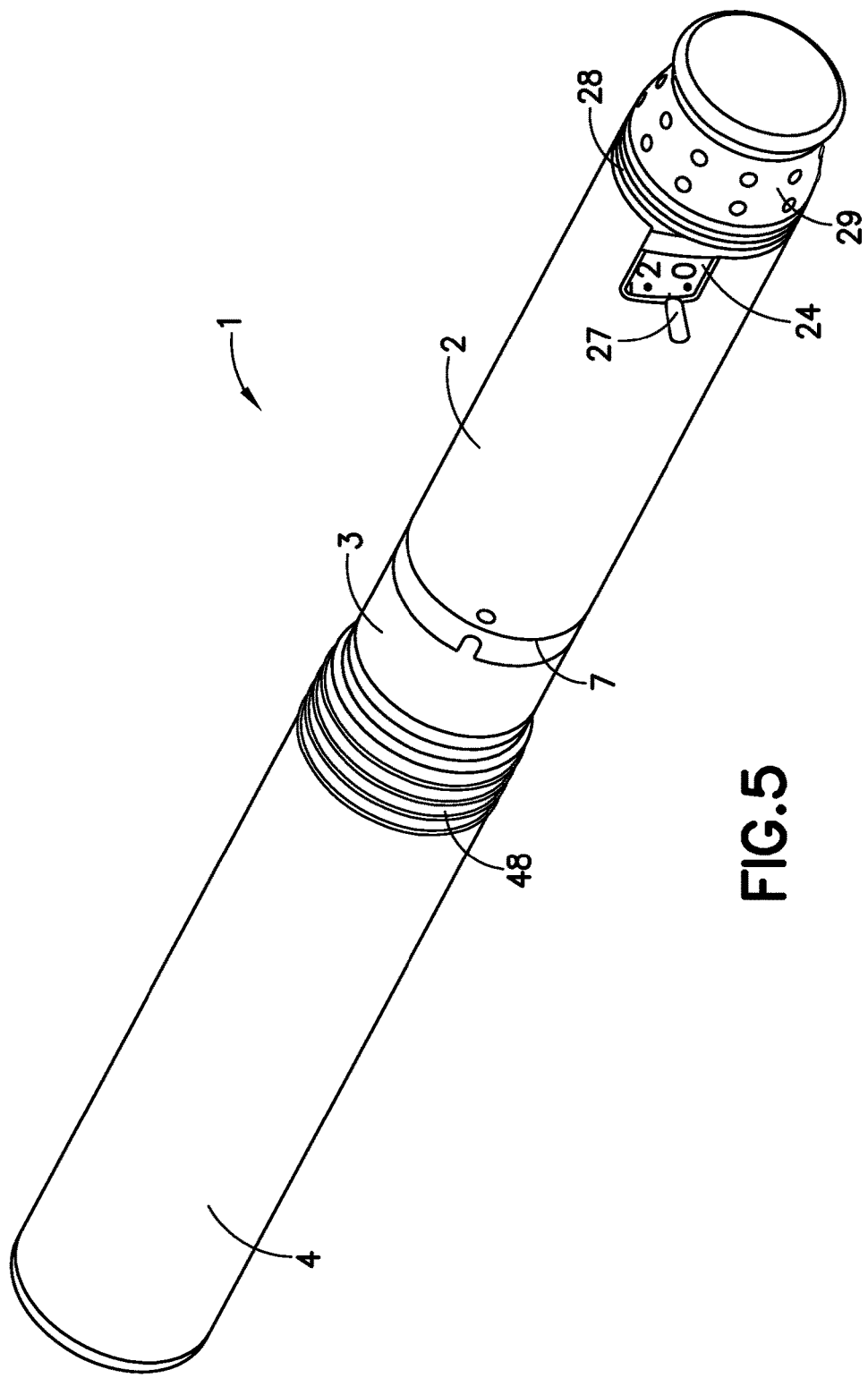
FIG. 5 is a perspective view of another embodiment of a drug delivery pen in accordance with the present invention.

FIG. 4 is a close-up view of the window 24 of the main body 2 of the self-injection device 1 of FIG. 1. The window 24 displays the amount of dosage of liquid medicament selected by the user via the dose setting device or knob 29. A window cover 26 surrounds the window 24, to visually highlight the window 24. The window cover 26 includes a pointer 27 that points in the direction of the dosage of liquid medicament corresponding to the dosage set by dialing the dose setting device 29. The dose setting device 29 is preferably a dial or knob including indents and dimples or small protrusions that assist a user in properly gripping the device.

The window cover 26, illustrated in FIG. 4, may be a separate component from the main body 2, or it may be over-molded onto the main body 2. Alternatively, the window cover 26 may be printed onto the main body 2. In any case, it is preferred that the window cover 26 be the same color as the dose setting device 29. Furthermore, it is preferred that the cover opening 260 in the window cover 26 be sized such that it is larger than the body opening 200 on the main body 2, to reveal portion 201. It is preferred that the body opening 200 be shaped such that the body opening 200 aligns with a helical path of numerals representing a dose dialed with the dose setting device 29. More preferably, the body opening 200 is an elongated slot oriented at the same angle as the helical path of the numerals to be displayed in the body opening 200.

In one embodiment of the present invention, as illustrated in FIG. 4, the opening 260 is a substantially circular opening, with the pointer 27 extending over parts of both the body opening 200 and the cover opening 260. One advantage of such an arrangement is that the portion 201 can be revealed to highlight the numerals within the body opening 200 by providing a contrasting foreground.

Figure 6:
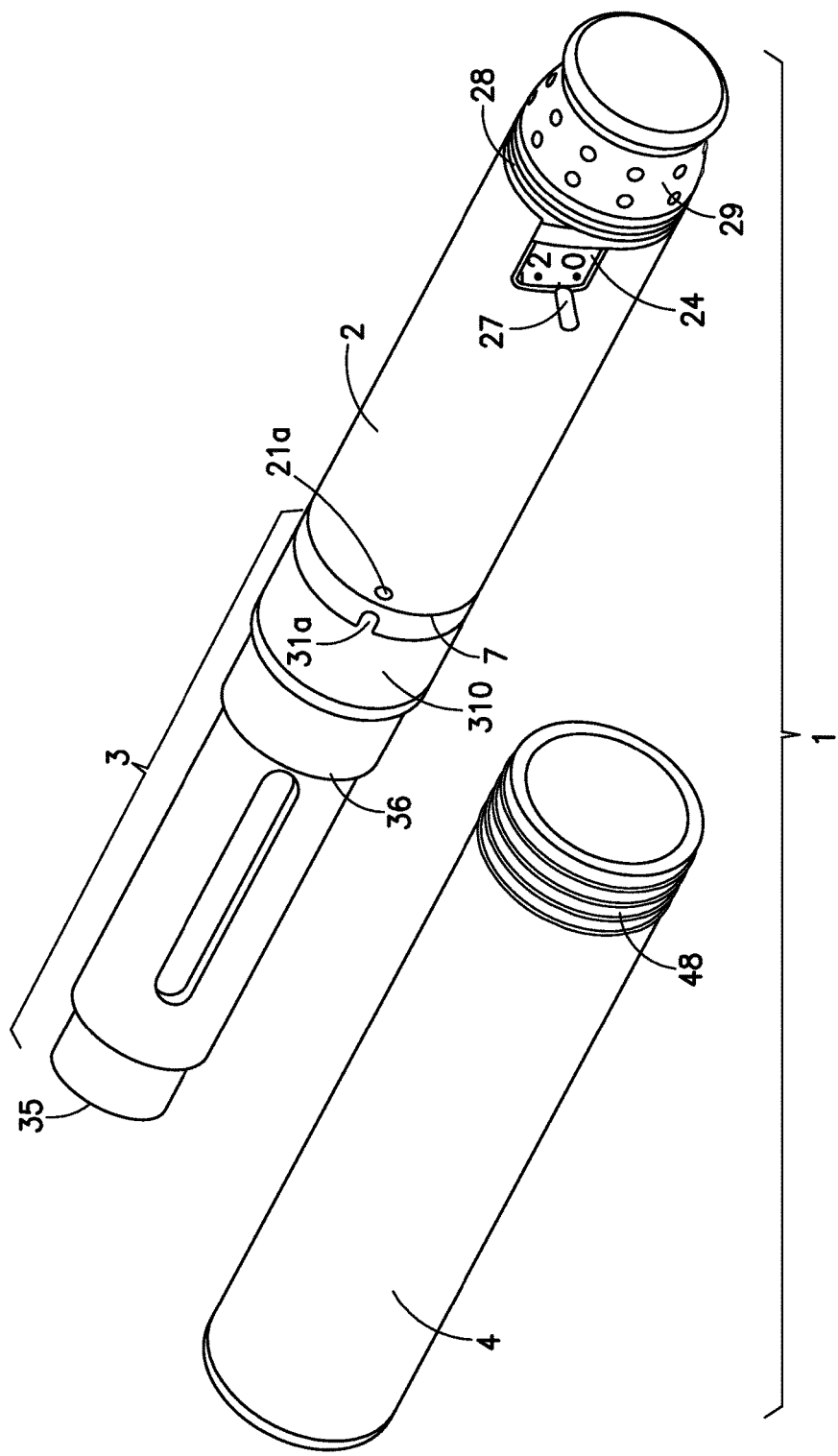
FIG. 6 is a perspective view of the drug delivery pen of FIG. 5 with its cap removed.
Figure 8:
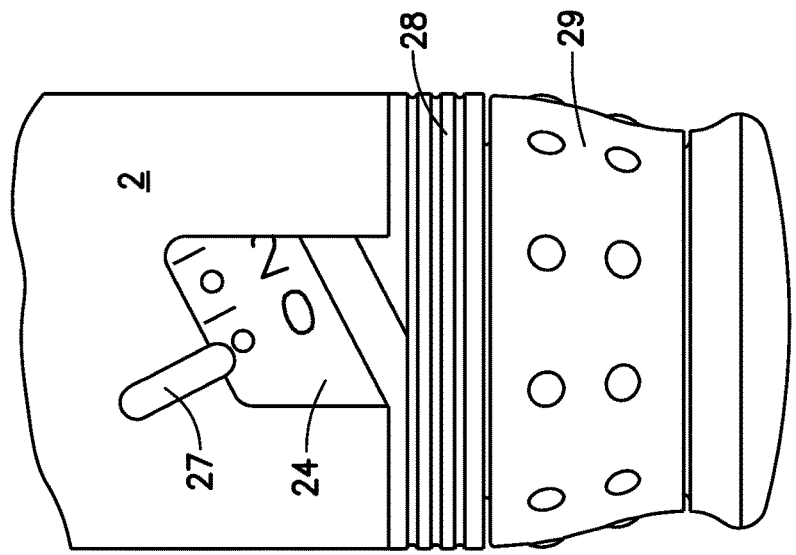
FIG. 8 is a close-up view of a display window for dosage of medicament to be delivered of the drug delivery pen of FIG. 5.
Figure 7:
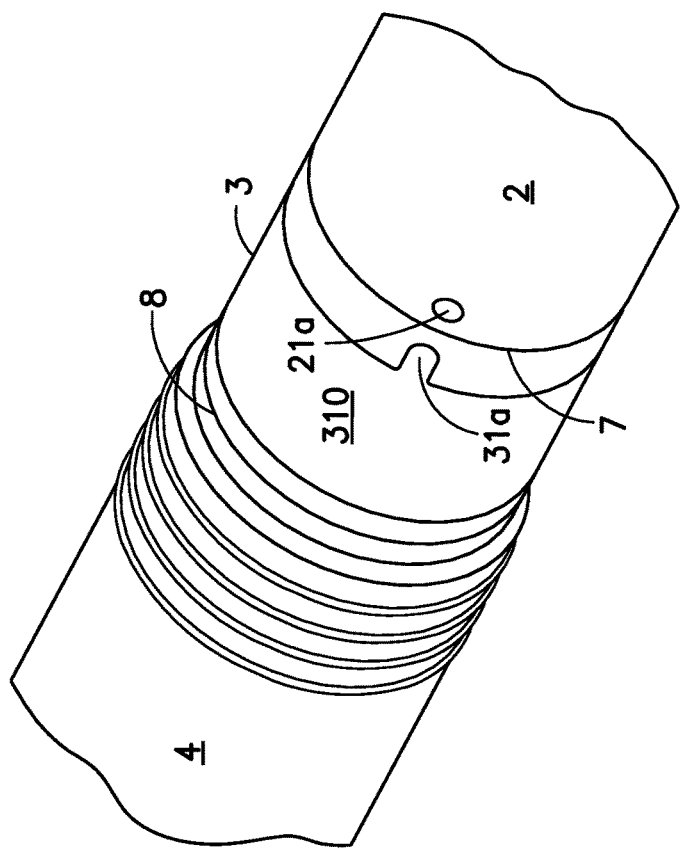
FIG. 7 is a close-up view of a visual indicator showing proper attachment of the medicament holder to the main body of the drug delivery pen of FIG. 5.

FIGS. 5-8 illustrate another embodiment of the self-injection device of the present invention. In this embodiment, the indicator mark on the cartridge holder 3 is an indicia 310 in the form of a cylinder, with a pointer 31a extending in a longitudinal direction of the self-injection device 1. When the cartridge holder 3 is properly attached to the main body 2, the pointer 31a of the cartridge holder 3 aligns with the indicator mark 21a of the main body 2, as illustrated in FIGS. 6 and 7. This embodiment also includes grip portions 28, 48 on the main body 2 and the cap 4, respectively, to visually highlight the self-injection device 1. In a preferred embodiment, the grip portions 28, 48 are made of a clear material. The embodiment of FIGS. 5-8 is similar to that of FIGS. 1-4 in the manner of attachment of the main body 2, the cartridge holder 3 and the cap 4.

Figure 9:
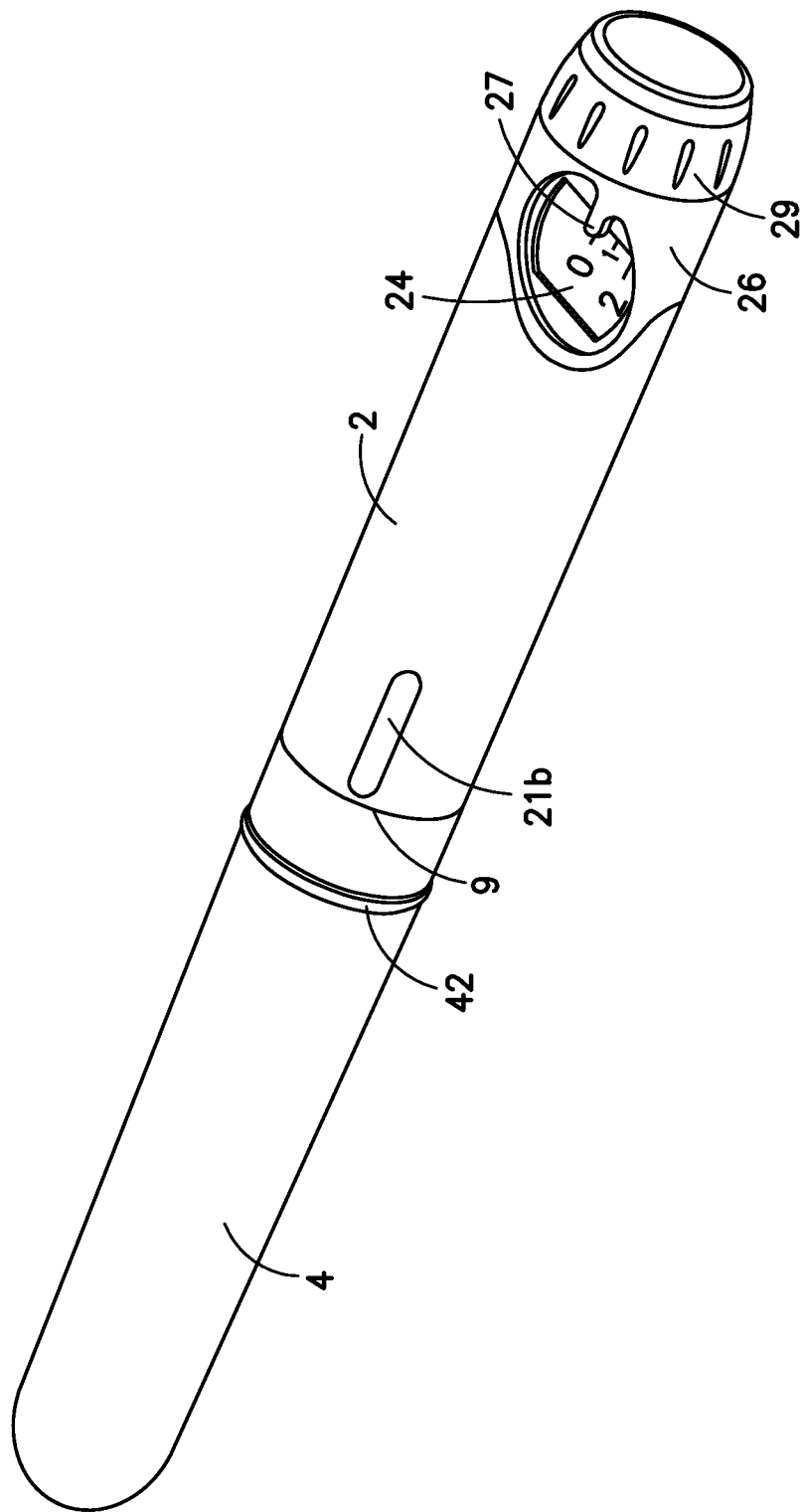
FIG. 9 is a perspective view of another embodiment of a drug delivery pen in accordance with the present invention.
Figure 10:
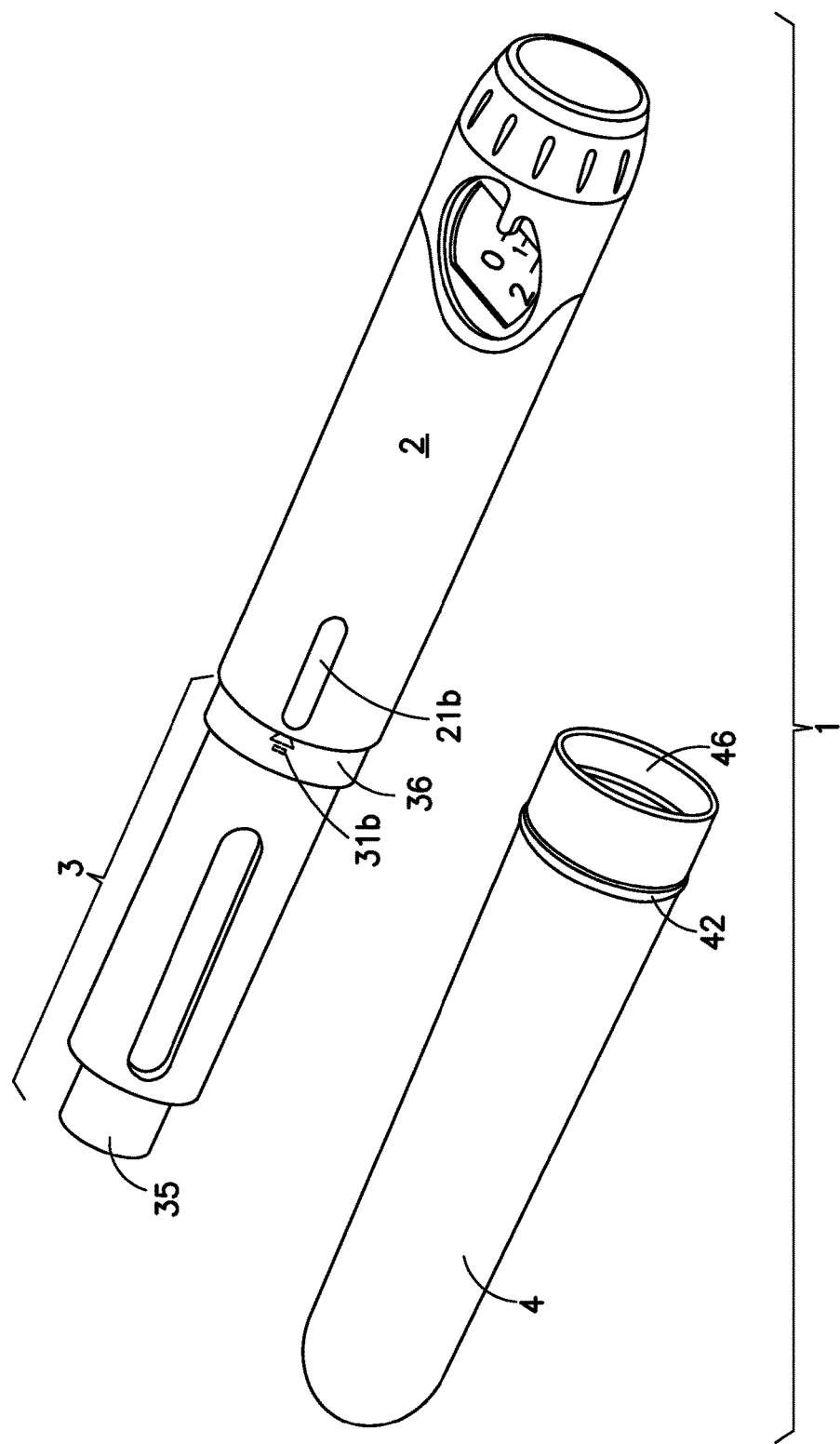
FIG. 10 is a perspective view of the drug delivery pen of FIG. 9 with its cap removed.
Figures 11, 12:
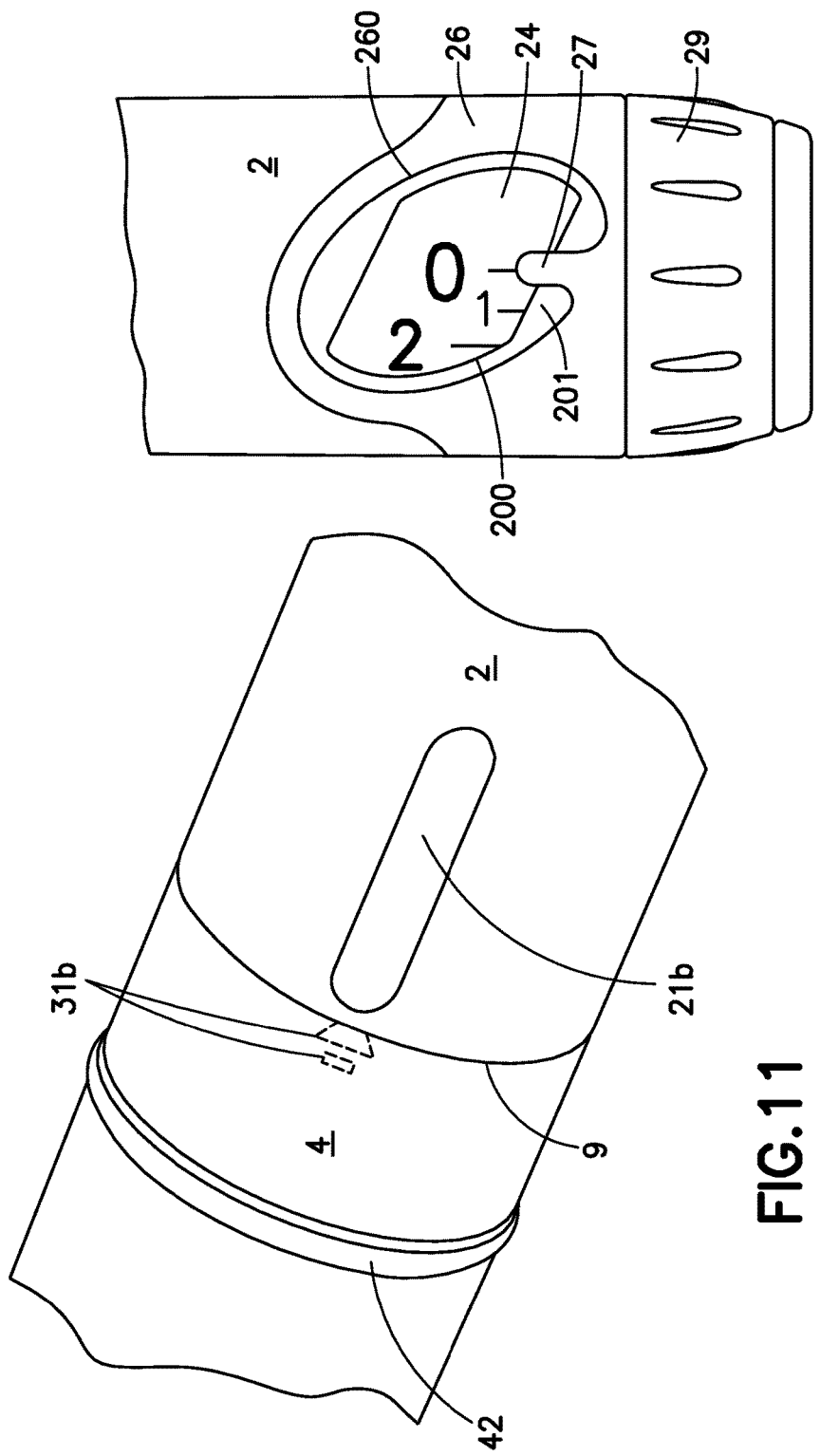
FIG. 11 is a close-up view of a visual indicator showing proper attachment of the medicament holder to the main body of the drug delivery pen of FIG. 9.
FIG. 12 is a close-up view of a display window for dosage of medicament to be delivered of the drug delivery pen of FIG. 9.

The embodiment of the self-injection device of FIGS. 9-12 differs from that of the embodiments mentioned above in several ways. In this embodiment, the cartridge holder 3 is fully covered by the cap 4 when the cartridge holder 3 is properly attached to the main body 2, as illustrated in FIG. 9. As illustrated in FIG. 10, the indicator mark 31b on the cartridge holder 3, in the form of an arrow, is aligned with the indicator mark 21b on the main body 2, in the form of a raised bar, to indicate that the two parts are properly connected. The cap 4 is made, at least partially, of a clear or translucent material so that even when the cap 4 is attached on the cartridge holder 3, the indicator mark 31b on the cartridge holder 3 is visible, as illustrated in FIG. 11. Line or gap 9 indicates the connection border between the cap 4 and the main body 2.

In the embodiment of FIGS. 9-12, the cap 4 fully covers the cartridge holder 3. The window cover 26 of the main body 2, surrounding the window 24, may be a separate component from the main body 2 or it may be over-molded onto body 2. Alternatively, the window cover 26 may be printed onto the main body 2. In any case, it is preferred that the window cover 26 be the same color as the dose setting device 29. Furthermore, as illustrated in FIG. 12, it is preferred that the window cover opening 260 in the window cover 26 be sized such that it is larger than the body opening 200 on main body 2, to reveal portion 201. Preferably, the body opening 200 is shaped such that the body opening 200 aligns with a helical path of numerals representing a dose dialed with dose setting device 29. More preferably, and as illustrated in this embodiment, the body opening 200 is an elongated slot having rounded edges oriented at the same angle as the helical path of numerals to be displayed in the body opening 200. In this embodiment, the cover opening 260 is a substantially oval opening, with the pointer 27 extending over parts of both the body opening 200 and the window cover opening 260. One advantage of such an arrangement is that the portion 201 can be revealed to highlight the numerals within body opening 200 by providing a contrasting foreground.

Although only a few exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the appended claims and their equivalents.

The invention claimed is:

1. A self-injection device comprising:
   a main body having a main axis and a distal surface, comprising a dose setting device;
   a cartridge holder having a proximal surface for holding a liquid medicament cartridge adapted to be threaded onto the main body such that the distal surface moves adjacent to the proximal surface, at least one of the cartridge holder and the liquid medicament cartridge comprising a needle receiving portion;
   a drive mechanism for applying force to the medicament cartridge to force liquid medicament from the cartridge according to a dose selected by the dose setting device; and
   a visual indicator comprising a first indicator mark on an external surface of the main body, located proximal of the distal surface, and a second indicator mark on the external surface of the cartridge holder, located distally of the proximal surface, that become rotationally aligned in the direction of the main axis for indicating that the main body and the cartridge holder are properly threaded together.

2. The self-injection device as claimed in claim 1, wherein the visual markings are elevated from the respective cartridge holder and main body.

3. The self-injection device as claimed in claim 1, wherein the visual markings are the same.

4. The self-injection device as claimed in claim 1, wherein the visual markings are different.

5. The self-injection device as claimed in claim 1, wherein the marking on the main body is raised and comprises a bar shape.

6. The self-injection device as claimed in claim 1, wherein the main body comprises a dose setting window for visually indicating to a user the dose of the medicament that is selected by manipulating the dose setting device.

7. The self-injection device as claimed in claim 6, further comprising an indicator mark on the main body aligned with the set medicament dosage to assist a user to set the desired medicament dose.

8. The self-injection device as claimed in claim 6, wherein the main body further comprises a cover surrounding the periphery of the dose setting window and an indicator mark extending from the cover toward the dose setting window to assist a user to set the desired medicament dose.

9. The self-injection device as claimed in claim 1, wherein the dose setting device is knob.

10. The self-injection device as claimed in claim 1, wherein the drive mechanism comprises a lead screw movably disposed within said cartridge and movably connected to the dose setting device.

11. The self-injection device as claimed in claim 1, wherein the medicament comprises insulin.

12. The self-injection device as claimed in claim 1, further comprising a cap for detachably covering a part of the cartridge holder.

13. The self-injection device as claimed in claim 12, wherein the visual indicator comprises a first visual marking on the cartridge holder and a second visual marking on the main body such that when the cartridge holder and the main body are properly connected, the visual markings are aligned.

14. The self-injection device as claimed in claim 13, wherein the cap comprises clear or translucent material such that the marking on the cartridge holder is visible when the cap is attached to the cartridge holder.

\* \* \* \* \*